US008684929B2

(12) United States Patent
Heaton

(10) Patent No.: US 8,684,929 B2
(45) Date of Patent: Apr. 1, 2014

(54) METHOD FOR VISUALIZING A CHRONOLOGICAL SEQUENCE OF MEASUREMENTS

(75) Inventor: Kelly Heaton, Ersigen (CH)

(73) Assignee: Roche Diagnostics International AG, Rotkreuz (CH)

( * ) Notice: Subject to any disclaimer, the term of this patent is extended or adjusted under 35 U.S.C. 154(b) by 1465 days.

(21) Appl. No.: 11/956,840

(22) Filed: Dec. 14, 2007

(65) Prior Publication Data

US 2008/0208027 A1    Aug. 28, 2008

(30) Foreign Application Priority Data

Dec. 14, 2006    (EP) ..................................... 06405518

(51) Int. Cl.
*A61B 5/00* (2006.01)
(52) U.S. Cl.
USPC ........................................................ 600/365
(58) Field of Classification Search
USPC .................... 600/365, 309, 345, 347; 345/44; 702/176–178
See application file for complete search history.

(56) References Cited

U.S. PATENT DOCUMENTS

| | | | | |
|---|---|---|---|---|
| 5,178,544 A | * | 1/1993 | Aleck | 434/262 |
| 5,396,886 A | * | 3/1995 | Cuypers | 600/301 |
| 2003/0069751 A1 | * | 4/2003 | Lichtenstein et al. | 705/2 |
| 2003/0125612 A1 | * | 7/2003 | Fox et al. | 600/347 |
| 2005/0038832 A1 | | 2/2005 | Feigenbaum | |

FOREIGN PATENT DOCUMENTS

| | | |
|---|---|---|
| CN | 1407734 | 4/2003 |
| EP | 1 283 023 A1 | 2/2003 |
| EP | 1283023 | 2/2003 |
| EP | 1283023 A1 | 2/2003 |
| EP | 1494158 A2 | 1/2005 |
| WO | WO 2006133348 * 12/2006 | ............. A61B 5/145 |

OTHER PUBLICATIONS

Strang, Gilbert. "Polar Coordinates and Complex Numbers". Calculus. Wellesley-Cambridge Press. pp. 348-350.*

(Continued)

*Primary Examiner* — Patricia Mallari
*Assistant Examiner* — Tiffany Weston
(74) *Attorney, Agent, or Firm* — Dinsmore & Shohl LLP

(57) ABSTRACT

The invention comprises a method for visualising a chronological sequence of measurements, in particular obtained from a continuous glucose monitoring (CGM) process, comprising the step of presenting measured data in polar coordinate graphing system. A device 100 is disclosed that comprises a measuring unit 101, in particular a continuous glucose measuring unit, a communication link 103 for transmitting the measured data, in particular a wireless transmission device with a sending 104 and a receiving part 105, and a display 110, optionally with a computing unit 107 that is designed and programmed to visualise data obtained from the measuring unit according to the previously described method, in particular a mobile phone display, MP3 player display, handheld computer display, laptop computer display, personal computer display or other display device being addressable by the communication link. The method and the device enable both the patient and the physician or HCP to improve their recognition of important and/or periodic events during a chronological sequence of (CGM) measurements.

20 Claims, 6 Drawing Sheets

(56) References Cited

OTHER PUBLICATIONS

Advanced Software Engineering. http://web.archive.org/web/20040204024141/http://www.advsofteng.com/gallery.html Published Feb. 4, 2004.*

Advanced Software Engineering. http://web.archive.org/web/20050216091832/http://www.advsofteng.com/gallery_line.html Published Feb. 16, 2005.*

Strang, "Polar Coordinates & Complex Numbers", Calculus, Wellesley-Cambridge Press, Box 82-279, Wellesley, MA, 1991, pp. 348-350.

Chart Gallery-Polar/Radar Charts, Advanced Software Engineering, downloaded Oct. 13, 2012, http://web.archive.org/web/20040204024141/http:/www.advsofteng.com/gallery.html, 2 pages, 2003.

* cited by examiner

METHOD FOR VISUALIZING A CHRONOLOGICAL SEQUENCE OF MEASUREMENTS

CROSS REFERENCE TO RELATED APPLICATION(S)

This application claims priority to European Patent Application No. 06 405 518.9, filed Dec. 14, 2006, which is hereby incorporated herein by reference in its entirety.

BACKGROUND

The invention relates to a method for visualising a chronological sequence of measurements, in particular obtained from a continuous glucose monitoring process. The invention further relates to a device for processing and visualising such a chronological sequence of measurements.

Monitoring parameters measured in or on the body of humans such as a concentration of a certain substance in a given body fluid has many applications. In particular, the monitoring is crucial in the context of therapies that involve an administration of active substances regulated depending on the value of one or a plurality of physiological parameters. A prominent example is diabetes therapy where the administration of insulin is effected depending on a measured glucose concentration in a body fluid of the patient.

Conventionally, diabetic patients who need to regularly administer insulin have periodically taken measurements of their blood glucose level, e.g. using a hand held strip-based glucose meter. However, the small number of measurements (usually four a day) provide only a very coarse picture of the progression of the glucose level ("snapshots" in time). They cannot give dynamic information about the metabolic response to a specific event such as a meal or physical activities of the patient; or more generally, the glucose trend during a period of time.

Continuous glucose monitoring (CGM) is a new technology for diabetes self-management. Instruments for continuous glucose monitoring record glucose concentrations over a period of time that lasts from several hours to several days, weeks or even months. The measurement frequency is much higher than that of the traditional spot blood glucose (bG) measurements referred to above, namely usually at least 10 measurements per hour. In principle, the increased temporal resolution provides the patient as well as his or her health care provider(s) (HCP) with a rich data set of time-variant glucose information. In principle, the continually measured glucose data can be used to more specifically adjust and refine the diabetes therapy to individual needs by adjusting the basal insulin rate as well as the timing and the amount of boluses. Furthermore, the data provides indications about advisable changes of the patient's behaviour, e.g. concerning different food choices (type, portion) or activity changes.

However, the advantages of CGM can easily be overwhelmed by the drawbacks of too much information. As CGM is a data-intensive method, visualising measured data in an intuitive way is crucial in order to allow easy interpretation of the measured data. The common way of visualising the measured data is by plotting curves in a Cartesian coordinate graphing system. In such a Cartesian coordinate graphing system one of the two axes (e.g. the horizontal x-axis) represents the progress in the measurement pattern, in particular this axis represents time. The other axis (e. g. the vertical y-axis) then represents the measured values, in particular the measured glucose level for each measurement. As time proceeds, an interpolated curve can be plotted from the measured data.

Multiple data sets of continuous glucose information, e.g. corresponding to different time periods such as three data sets of the same patient taken on three different days, can be graphically overlaid for the purpose of comparison and pattern recognition. However, comparing such overlaid curves is difficult due to the complexity of the corresponding graphical representation. Furthermore, physicians (or other health care providers carrying responsibility for a patient's therapy) are primarily interested in a few key aspects of diabetic health that may not be immediately apparent in the visual confusion of a complex Cartesian line graph. In the case of diabetes therapy, among these key aspects are: The relative time spent in hyper- versus hypoglycemia; the intensity of hyper- and hypoglycemic events; and tendencies for a patient to have glucose excursions during certain times of day, or certain days of the week.

Moreover, the average patient is usually unable to interpret the measurements being performed at his/her body. As recognition and attribution of certain shapes in the presented data to certain events during the measurement pattern plays a key role in a successful diagnosis process, improving the visualisation of the measured data is important. To recognise important aspects of a measurement pattern such as e.g. the relative time spent in hyper- and hypoglycemia and the intensity of hyper- and hypoglycemic events a patient or a physician needs further analysis of the curve(s) shown in a Cartesian coordinate graphing system.

SUMMARY

It is the object of the invention to create a method as well as a device pertaining to the technical field initially mentioned, that enables both the patient and the physician to improve their recognition of important and/or periodic events during a chronological sequence of measurements.

The solution of the invention is specified by the features of claims 1 and 14, respectively. According to the invention, the method of visualising a chronological sequence of measurements comprises the step of presenting the measured data on a polar coordinate graphing system. This task may be performed using a device comprising a measuring unit, in particular a continuous glucose measuring unit, a communication link for transmitting the measured data, in particular a wireless transmission device with a sending and a receiving part, and a display, optionally with a computing unit, that is designed and programmed to present the measured data on a polar coordinate graphing system. The display is in particular a mobile phone display, MP3 player display, handheld computer display, laptop computer display, personal computer display or other display device being addressable by the communication link.

As a Cartesian coordinate graphing system by nature consists of two or more axes, which extend to infinity, such a system does not represent the periodic nature of certain aspects of the human physiology. Many factors that influence e.g. the glucose level occur regularly and periodically. Cartesian coordinate graphing systems therefore are not an intuitive way of visualising measured data. The analysis results of the measured data e.g. during diabetes therapy are not satisfactory due to a rather difficult detection of factors that influence the glucose level such as a meal or physical activity. Especially the periodicity of such events is not sufficiently considered in a visualisation by a Cartesian coordinate graphing system. Furthermore, the Cartesian coordinate graphing system does not allow the patient or his/her HCP to easily recognise events that are important.

Presenting the measured data in a polar coordinate graphing system improves the physician's as well as the patient's ability to evaluate and recognise respectively key aspects of data e. g. obtained from CGM. Considering the fact that during CGM many important events such as meals or physical activities occur regularly or periodically, the periodic nature of a polar coordinate graphing system is of great advantage.

The invention is not limited to visualising continuous glucose data of a specific duration or frequency, but may be broadly applied to any time-varying glucose signal or even to other chronological sequences of measurements that show certain periodicities. The method is appropriate for retrospective glucose data analysis as well as for real-time applications.

The circular axis of a polar coordinate graphing system shows a periodic nature. It is in so far useful to plot the chronologically changing parameter, e.g. the time of the measurement, along the circular axis. Hours per day, days per week, weeks per months or combinations thereof are examples of sectioning the circular axis in order to gain an intuitive overview of the CGM data. By plotting the time along the circular axis, regularly or periodically occurring events such as e.g. breakfast, lunch or dinner which usually occur regularly once a day or e.g. sports activities, which perhaps are performed on a regular basis on certain days of the week, can be recognised much easier than in a Cartesian coordinate graphing system. One could also think of plotting e.g. the number of measurements along the circular axis. This would easily show a periodicity of events with respect to the number of measurements.

The measured values are preferably plotted along the radial axis. Regions of the graph corresponding to values of higher amplitudes along the radial axis appear disproportionately big, due to the distortion of a curve along the circular axis as the curve is moving away from the origin of the polar coordinate graphing system. Because of this visual artefact of the polar coordinate graphing system, the importance of events that lead to such high amplitudes is highlighted in an intuitive way. In particular plotting the glucose concentration during CGM along the radial axis leads to a highlighting of parts of the curve which show particularly high values and could therefore be medically critical.

A device using the previously described visualisation method should comprise a measuring unit which collects the data to be visualised, in particular a CGM unit. In addition a communication link for transmitting the measured data is necessary. Advantageously this can be a wireless transmission device with a sending and a receiving part. A display, optionally equipped with a computing unit that is designed and programmed to visualise data obtained from the measuring unit then can present these data in the described way. Such a display can be one especially designed for visualising CGM data or e.g. a mobile phone display, MP3 player display, handheld computer display, laptop computer display, personal computer display. These and any other display, which is addressable by the transmission device, can be used, optionally in connection with a computing unit, to present the measured data.

The polar coordinate graphing system advantageously features a graphical highlighting of critical boundaries of the performed measurement. In particular for CGM, the thresholds of hyper- and hypoglycemia respectively can be represented by graphical means such as coloured or grey shaded lines or areas, bold lines, grids or similar features.

An advantageous feature of the visualisation method is that numerical values of different numerical ranges are presented in different colours or grey shades. This simplifies the recognition of situations, where the measured values reach certain numerical ranges, e.g. when the measured glucose level reaches a numerical range which might be hazardous to the patient's health. Either the colour of the full curve presented or the part of it reaching that numerical range could be changed.

Another advantageous feature of the visualisation method is that the measured values can be plotted in different coordinate systems, whereas two (or more) coordinate systems can be displayed simultaneously. It is advantageous for recognition and understanding of the measured data if values above a reference value are displayed separately from those below that or another reference value. In case of CGM, values that indicate hyper- and hypoglycemia respectively are of particular interest. Therefore, it might be useful to plot those parts of the measured glucose level, which indicate hyperglycemia in a first coordinate system and those parts of the measured glucose level, which indicate hypoglycemia in a second coordinate system. In the first coordinate system showing the numerical range of hyperglycemia the radial axis is annotated with increasing numbers, whereas in the second coordinate system showing the numerical range of hypoglycemia the radial axis is annotated with decreasing numbers. This method of visualisation also leads to the previously mentioned effect that medically critical or in general important situations (very high glucose levels as well as very low glucose levels) are always highlighted due to the special nature of a polar coordinate graphing system that these parts of a curve further away from the origin of the coordinate system appear disproportionately big. As both numerical ranges are of particular interest, both coordinate systems might be shown simultaneously in particular by overlaying one coordinate system by the other one, both the systems having a common circular axis (time) but differently scaled radial axes (numerical value of the measured parameter).

In this context the presentation of the difference of a measured value to a reference value might be of more intuitive or more practical meaning than an absolute value. Also the presentation of the modulus of such a difference might be clearer and more intuitive than the positive as opposed to the negative value of the difference. Therefore, the presentations of curves representing such a difference or the modulus of it are other advantageous features of the described visualisation method. In order to permit differentiation between time intervals during which the reference value is exceeded from time intervals during which the measured value falls below the reference value the corresponding regions of the graph may be highlighted in a different way (e.g. employing colours, shades, hatchings etc.).

The fact that a polar coordinate graphing system is periodically in its radian axis is advantageous for the presentation of data, which might also show some periodic or regular nature. In the example of CGM the periodicity of the radian axis advantageously matches periodicities in human medical cycles such as a day, a week or a month. The parallels of a polar coordinate graphing system to an analogue clock make recognition of daily periodic events such as meals particularly easy. Therefore, a radian of $2\pi$ advantageously represents a period of time of 12 hours or 24 hours, so that the distribution of important or interesting events over such a period can be recognised particularly easy, at one glance. If a radian of $2\pi$ represents e.g. a week or a month, the influence of physical activities such as e.g. regular sports or other weekly or monthly events, which might affect the glucose level, can be recognised much easier compared to other visualisation methods that do not use one or several periodic axes. A device for processing and visualising the measured data may be designed and programmed in such a way that the periodicity of the radian axis is switchable, i.e. from 12 hour to 24 hour and 1 week intervals each corresponding to a radian of $2\pi$.

In a further advantageous visualisation mode a radian of $2\pi$ represents a fixed period of elapsed time, and data of this fixed period is displayed. Preferably, the fixed period of elapsed time matches a likely periodicity of the measured data, e.g. corresponds to the last 12 hours or 24 hours respectively. In this visualisation mode the axes of the polar coordinate graphing system remain fixed so the displayed data can be read similar to an analogue clock. The curve is moving advantageously clockwise along the circular axis and replaces or covers that part of the curve, which has been measured one period before. An advantage of this way of presenting data is that this visualisation method always provides an overview of the measured data of the last and therefore most actual period of time.

In the proceeding of continuously measured data, trends usually are one of the most valuable aspects being gained from the measurement. Therefore, interpolation of the data points is another advantageous measure of the previously described method of visualisation. This interpolation takes into account that usually not every single point is of importance. By interpolating the set of data points to create a smooth curve, important trends in the proceeding of the continuous measurement e.g. the CGM become clearer as rather unimportant fluctuations e.g. due to inaccuracies of the measurement process, mainly disappear.

A further advantageous aspect of the previously described visualisation method is colouring or grey shading of the area between the origin of the polar coordinate graphing system and the plotted curve. This feature supports the previously described effect that parts of a curve that are related to high values along the radial axis appear disproportionately big as the size of filled objects may be more easily assessed than the extension of stretched curves. Moreover, different coloured areas under each curve, where each colour is related to one curve can simplify the identification of different curves compared to the identification of curves, which are plotted as a coloured line only.

Another advantageous feature of the previously described visualisation method is to display the curves and the areas between the curves and the origin of the polar coordinate graphing system in such a way that these elements have a transparency. This effect is particularly useful for the visualisation of measurement sequences, which last for longer periods of time than the periodicity of the displayed polar coordinate graphing system, as the transparency allows for perceiving graphs concerning the previous revolutions that would otherwise be covered by the graph of the most actual revolution. Advantageously, the transparency effect leads to a gradual darkening of the covered area with every subsequent revolution. This consequently highlights those areas covered more frequently compared to those covered infrequently. The use of these transparency effects in combination with the periodicity of a polar coordinate graphing system helps recognising events which are of particular importance and that happen more or less periodically. As an example, in CGM periodic increases or decreases of the measured glucose level can be detected quite simply.

A further advantageous feature of the invention is to store numerous curves or sets of curves and display a selection or single ones of them at the request of the user or its HCP. This might be particularly useful for long-term monitoring of glucose levels and their development over a period of time. Thus advances in therapy or long-term effects of e.g. a diet can be found out individually. Furthermore, the actual glucose progression may be compared to stored "reference" progressions.

Preferentially, it is also possible to calculate an individual averaged curve representing the monitored parameter, e.g. glucose concentration, from previously recorded and stored data. Such an averaged curve can be used as reference curve for future measurements. For this purpose, it is advantageous if the averaged curve may be stored and later on displayed on the display, simultaneously with the actual progression of the monitored value.

This feature takes into account that each patient has an individual "normal" curve e.g. of glucose concentration that is different from a curve of an "average patient". Moreover, instead of or additional to a single averaged curve, a band of noncritical values or curves may be displayed being calculated from previously recorded and stored data by applying statistical methods to recorded and stored sets of curves (corresponding to noncritical progressions). Such a band of noncritical values does advantageously define a reasonable range of values e.g. of glucose concentration, which are considered to be noncritical. As the width of such a band of values might be varying over a day, which e.g. can be caused by varying types and/or amounts of food or different physical activities, an individual band of noncritical values matches the needs of a patient much better than a fixed range of noncritical values evaluated from an "average patient" or taken from a theoretical table. Preferably, the individual average curves or ranges are generated under the supervision of the responsible HCP.

Other advantageous embodiments and combinations of features come out from the detailed description below and the totality of the claims.

BRIEF DESCRIPTION OF THE DRAWING(S)

The drawings used to explain the embodiments show:

Figure 3:
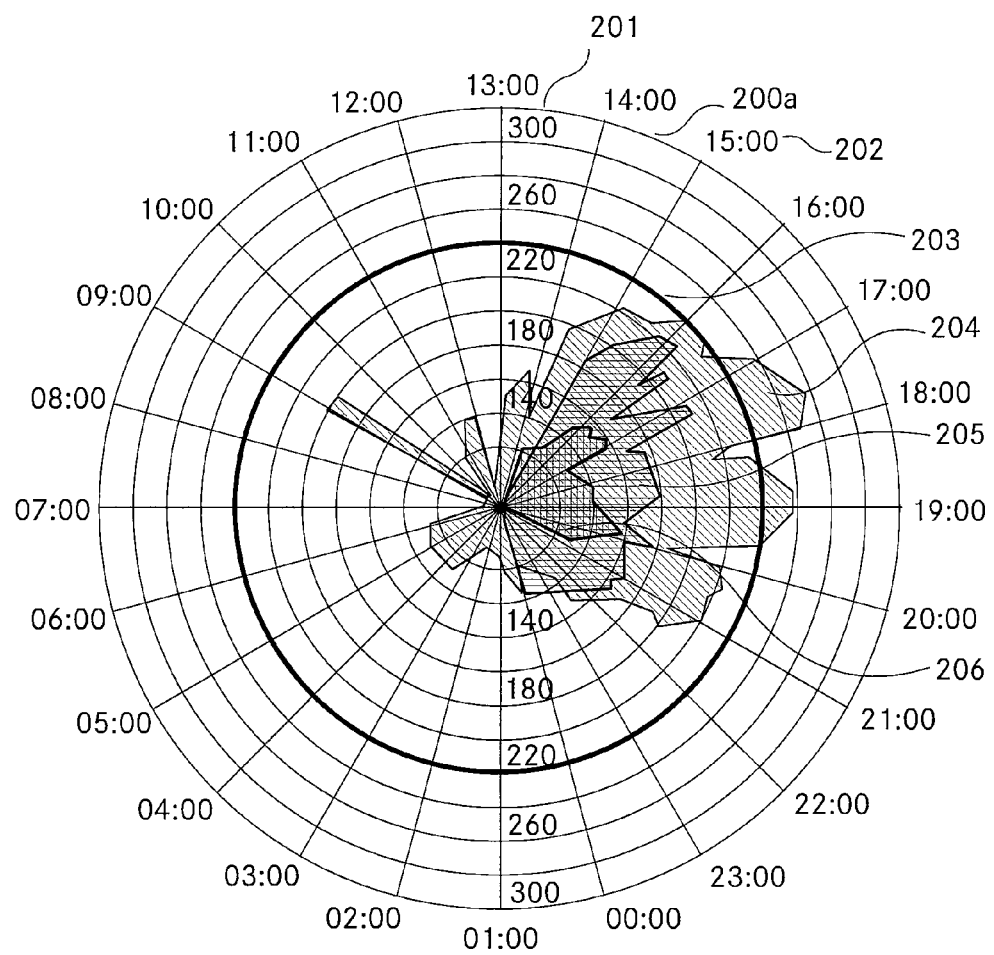
FIG. 3 is a diagram of an inventive polar coordinate graphing system for visualising a chronological sequence of measurements showing a display mode which allows for easily recognising hyperglycemia.
Figure 4:
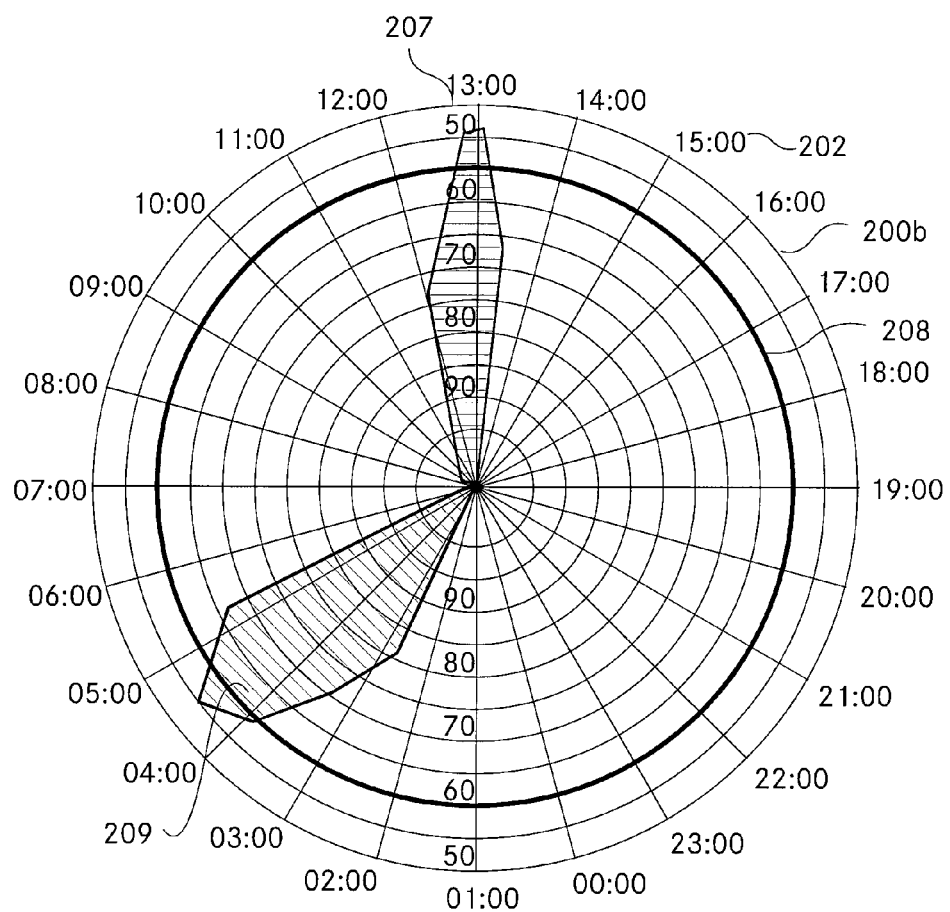
FIG. 4 is a diagram of an inventive polar coordinate graphing system for visualising a chronological sequence of measurements showing only values below a certain reference value.
Figure 5:
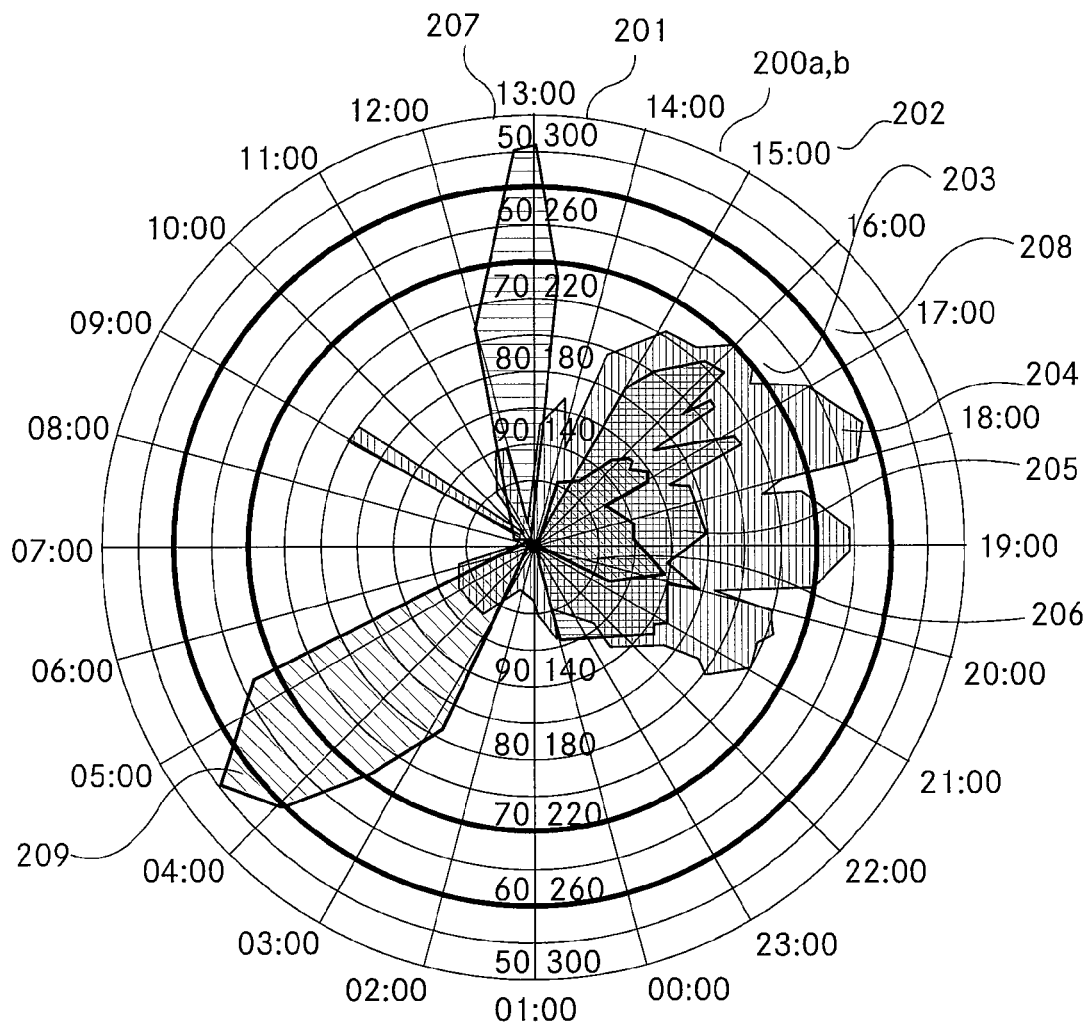
Figure 6:
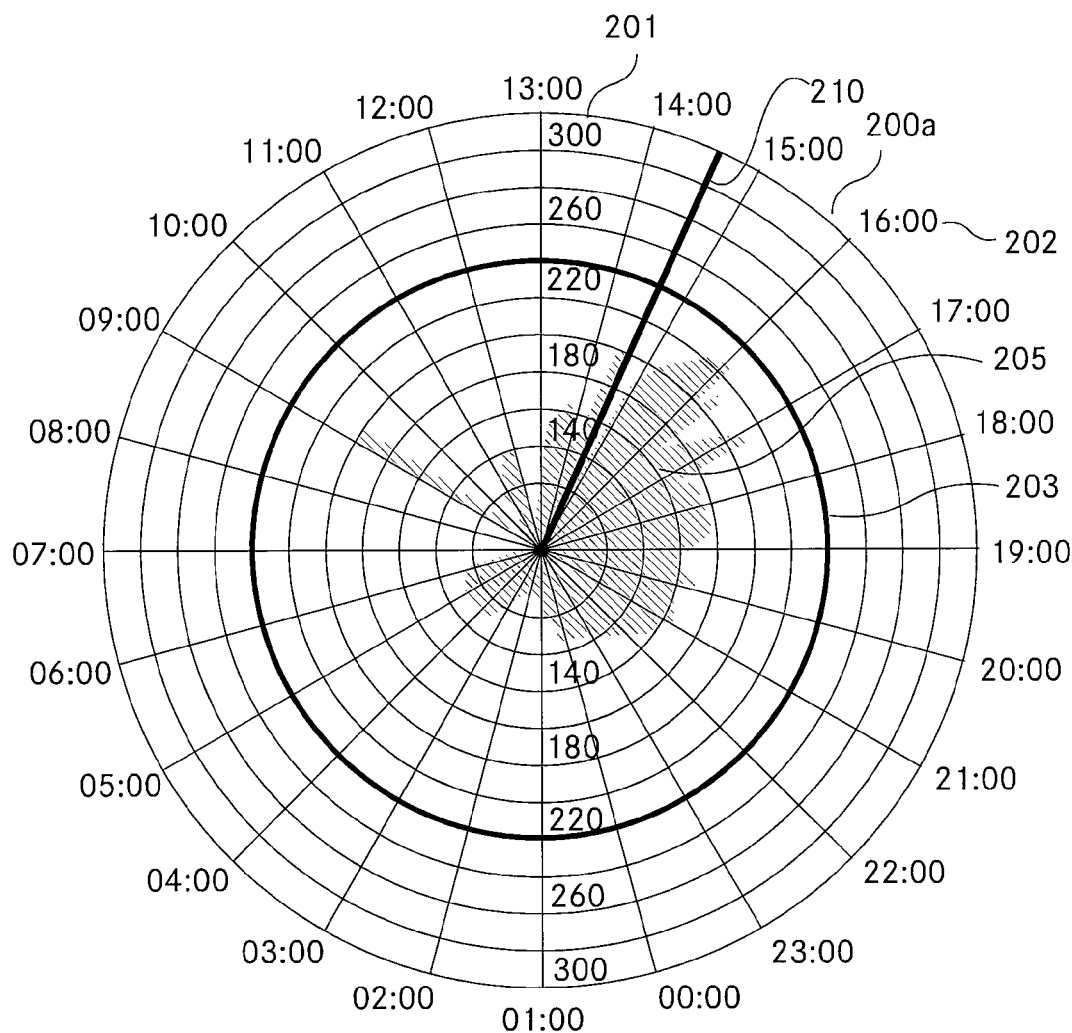

FIG. 5 is a diagram of two inventive polar coordinate graphing systems for visualising a chronological sequence of measurements showing the coordinate systems presented in FIGS. 3 and 4 simultaneously; and FIG. 6 is a diagram of an inventive polar coordinate graphing system for visualising a chronological sequence of measurements where a radian of $2\pi$ represents a fixed period of elapsed time of the last 24 hours.

In the figures, the same components are given the same reference symbols.

DETAILED DESCRIPTION

Figure 1:
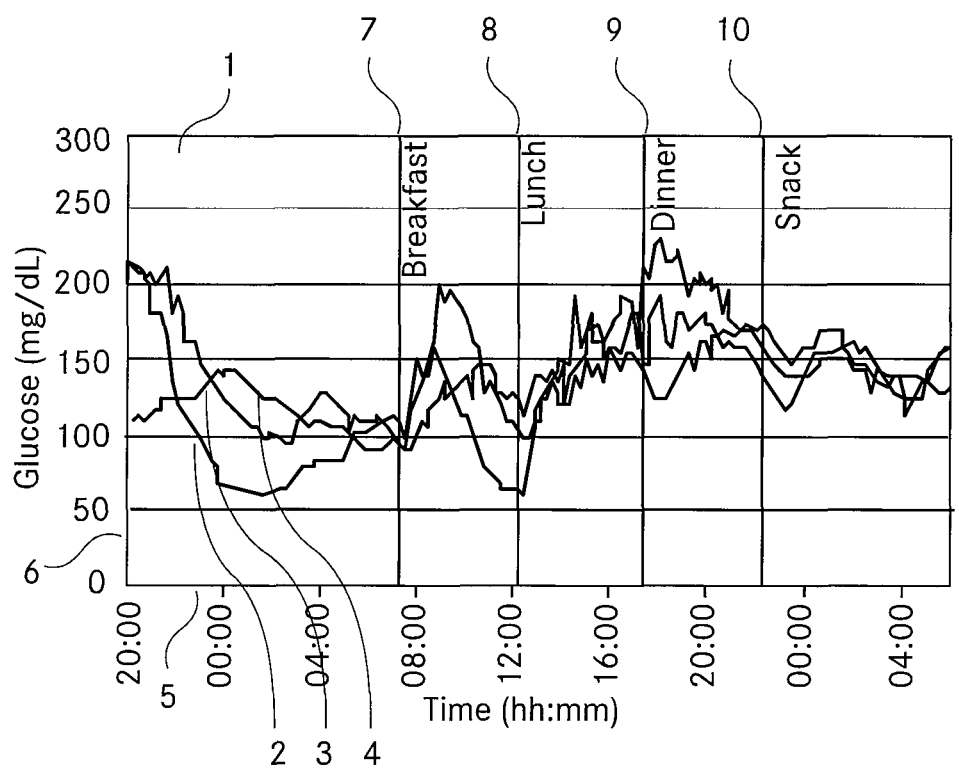
FIG. 1 is a diagram of a Cartesian coordinate graphing system visualising a chronological sequence of measured glucose concentrations.

FIG. 1 shows a diagram of a Cartesian coordinate graphing system 1 visualising three sets 2, 3, 4 of subsequently measured glucose concentrations of one patient. The horizontal axis 5 is annotated by the time at which the measurement has been performed whereas the vertical axis 6 is annotated by the measured glucose concentration (in units of mg/dl). The plotted data start at 20:00 of the previous day and stop beyond 04:00 of the following day. As can be seen from FIG. 1, due to the linear nature of the Cartesian coordinate graphing system 1, there is no visual highlighting of important events such as the crossing of a threshold to hyper- or hypoglycemia. Additionally, changes in the glucose concentration level of a patient depend on events such a meal or physical activities, which occur regularly. This regularity is not reflected by the Cartesian coordinate graphing system 1. For better understanding, the chronological positions of four meals are marked as vertical lines 7, 8, 9, 10. However, the effect of a meal on the glucose level cannot be easily determined from the Cartesian coordinate graphing system 1. Periodic events (e.g. lunches at about noon etc.) cannot intuitively be recognised. The data presented in FIG. 1 is used in FIGS. 3, 4, 5 and 6 as well, reduced to a selection meeting the coordinate graphing system respectively.

Figure 2:
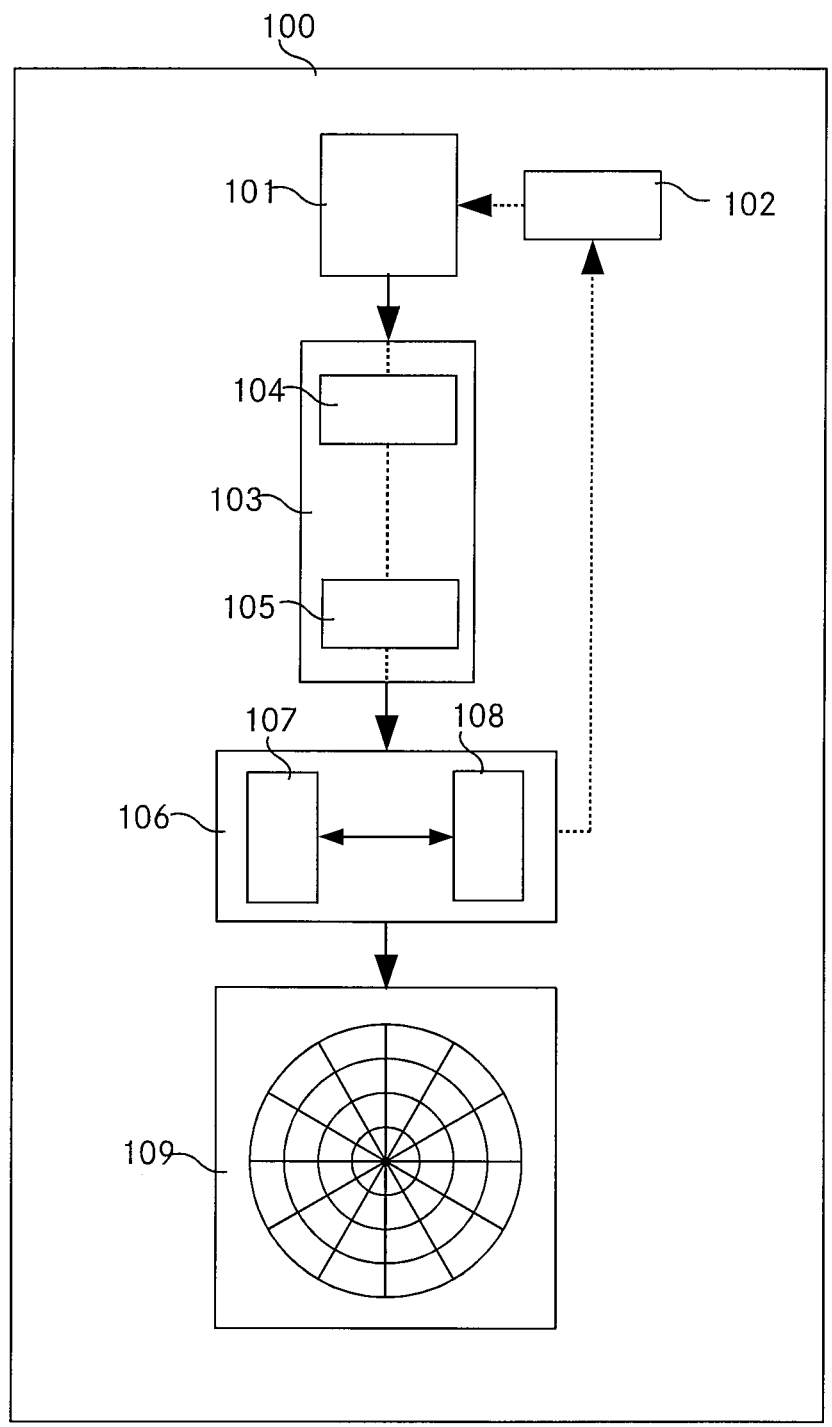
FIG. 2 is a schematic representation of an inventive device for measuring, processing and displaying a chronological sequence of measurements of a glucose concentration.

FIG. 2 shows a schematic representation of an inventive device 100 for measuring, processing and displaying a chronological sequence of measurements of a glucose concentration (continuous glucose monitoring CGM). The device 100 comprises a glucose meter 101, which performs the actual measurement of the glucose level in the interstitial fluid. The glucose meter 101 can optionally be connected to a control device 102, in particular a receiver of a remote control device, which controls e.g. the frequency of measurements or the time when these are performed. The glucose meter 101 is connected to a data processing device 106 by means of a communication link 103. The communication link 103 can in particular contain a wireless transmission device, which comprises a sending unit 104 and a receiving unit 105. The communication link 103 is connected to a data processing device 106, which contains a computing unit 107, which optionally can be developed and programmed to apply various statistical calculations on recorded data, and a data storage unit 108, which can be capable of storing numerous curves. The data processing device 106 optionally is connected to the control device 102, which is controlling the glucose meter 101. The data processing device 106 can be a device specifically developed for processing data of a glucose meter or any other technical means being programmable for processing and storage of data such as PDAs, modern mobile phones or computers. The processing unit 106 is connected to a display 109 on which a chronological sequence of measurements obtained from the measuring unit 101 may be displayed. The display of a PDA or mobile phone, especially but not exclusively if such a device is also used as the data processing unit, is a preferred means for displaying the processed data.

FIG. 3 shows a diagram 200a of an inventive polar coordinate graphing system for visualising the same set of measured data being visualised in FIG. 1. Along the radial axis 201 glucose concentration is plotted, starting from a value of 100 mg/dL, which has been chosen as reference value indicating a "normal" or target glucose level, and with increasing values up to as much as 320 mg/dL as the radius increases. The circular axis 202 is annotated by time and divided into 24 sections, each section representing a period of time of one hour. A highlighted circle 203 at a glucose level of 240 mg/dL marks a critical threshold of the glucose concentration which should not be exceeded. When a glucose level of more than 100 mg/dL is measured at a certain time, an appropriate point is plotted in the polar coordinate graphing system, where measurements following one another are connected by a line, which optionally can be interpolated providing a smoother curve. Measurements of glucose levels of less than 100 mg/dL lead to a point in the origin of this polar coordinate graphing system as there is no negative radial axis.

In that polar coordinate graphing system three subsequent revolutions 204, 205, 206 of measurements corresponding to a full day each are plotted, where in this figure each revolution is represented by an individual hatching. Instead of hatchings, different colours, intensities or grey shades may be employed, optionally provided by a transparency so multiple covering of an area leads to gradual darkening, colour change or superposition of different hatchings and is therefore easy to recognise. This is to intuitively indicate periodically occurring changes in the glucose level of a patient such as those caused by regular meals. A crossing of the highlighted circle 203 is an indication of hyperglycemia. This event appears particularly "alarming" as due to this particular artefact of a polar coordinate system the size of a part of a curve at higher distances from the origin looks bigger than one in the origin's vicinity.

Hyperglycemia sets in during the first revolution 204 between 16:40 and 18:00 and 18:20 and 19:30. It is easy to recognise that the shapes of the three revolutions 204, 205, 206 look similar to one another between 13:00 and 01:00 but show different levels of glucose concentration. From studying the diagram, the patient or his or her HCP respectively may recognise that there is a potential danger of hyperglycemia in a timespan from 15:45 until about 21:00. Furthermore, if the diagram is used in real-time the user may easily recognise if the glucose level proceeds approximately as during the other days or if it exceeds the values measured on earlier days at the same time of day.

One possible realisation of an individual average curve is to calculate the arithmetic mean of the curves corresponding to the three revolutions 204, 205, 206. This gives a more general trend in the curve progression. Similarly, by using the variability of the set of curves at each time, a band of noncritical glucose concentrations can be calculated and displayed. Thus the patient gets an idea of the regularities and periodicities of the daily glucose cycle and may more easily decide whether the current progression of the glucose concentrations might indicate upcoming trouble.

FIG. 4 shows a diagram 200b of an inventive polar coordinate graphing system visualising the same set of measured data being visualised in FIG. 1 but showing only glucose concentrations below 100 mg/dL. The radial axis 207 is annotated by the measured glucose concentration and has a negative direction. That means the radial axis starts in the centre of the coordinate system with its highest value of 100 mg/dL, which has been chosen as reference value indicating a "normal" or target glucose level, with its annotations decreasing to as low as 45 as the radius increases. The circular axis 202 is annotated by time and divided into 24 sections, where each section stands for a period of time of one hour. A highlighted circle 208 marks a critical glucose concentration of 55 mg/dL below which the glucose concentration should not fall. A curve crossing this highlighted circle indicates hypoglycemia and appears particularly "alarming" as the size of a part of a curve at higher distances from the origin looks bigger than one in the origin's vicinity. The glucose concentration measured at a certain time leads to a point plotted into the polar coordinate graphing system with points of successive measurements being connected to one another and so forming a curve. Optionally the connections of following points are interpolated in providing a smoother curve. A coordinate system as shown in FIG. 3 does only indicate measurements by a curve 209 when the glucose concentration has fallen below a value of 100 mg/dL. Values above 100 mg/dL are not plotted but as points in the origin of the polar coordinate graphing system as there is no positive radial axis. This enhances clarity in the visualisation of selective data and therefore makes diagnosis of hypoglycemia particularly easy. The plotted curve 209 shows two hypoglycemic events at between 03:50 and 04:40 and between 12:40 and 13:20 respectively. These two events correspond to two different measurement cycles which becomes clear from the different hatchings of the enclosed areas.

FIG. 5 shows the two diagrams 200a, 200b of two inventive polar coordinate graphing systems as presented in FIGS. 3 and 4 simultaneously. The combined radial axis 201, 207 is annotated by glucose concentration values, which are exceeding a common reference value of 100 mg/dL as well as by glucose concentration values, which are falling below that reference value, which has been chosen as being a "normal" or target value. The circular axis 202 is annotated by time and divided into 24 sections, where each section stands for a period of time of one hour. Each of the coordinate systems includes a highlighted circle 208, 203, at 240 mg/dL and 55 mg/dL respectively, which mark critical glucose concentration thresholds to hyper- and hypoglycemia respectively.

The two diagrams of FIGS. 3 and 4 are laid over one another keeping the time axes equally scaled providing a complete set of data, as opposed to one of the two polar coordinate graphing systems of FIGS. 3 or 4, where only glucose levels below and above 100 mg/dL respectively have been plotted. FIG. 5 moreover indicates the "importance" of the measured glucose concentration levels in the same intuitive way as each of the two diagrams as the target value lies in the origin of the combined diagram and "normal" (noncritical) values lie in the vicinity of the origin where the areas enclosed by the curve are small. Therefore, the crossing of one of the two highlighted circles 203, 208 representing critical glucose concentration values does also look as "alarming" as in one of the diagrams of FIGS. 3 or 4.

In this diagram each of the curves corresponding to the revolutions 204, 205, 206, 209 is represented by an individual hatching. Instead of hatchings different colours, intensities or grey shades may be employed, optionally provided by a transparency so multiple covering of an area leads to gradual darkening, colour change or superposition of different hatchings of it and is therefore easy to recognise. If so, preferably the highlighted circles 203, 208 are shown in the same colour as the related curves, e.g. red for the threshold to hyperglycemia if curves of values above 100 mg/dL are plotted in red shades as opposed to blue for the threshold to hypoglycemia if curves of values below 100 mg/dL are plotted in blue shades.

FIG. 6 shows a diagram 200 of a polar coordinate graphing system where the radial axis 201 is annotated by the measured values of glucose concentration starting from a value of 100 mg/dL, which has been chosen as reference value indicating a "normal" or target glucose level, and with increasing values as the radius increases. The circular axis is annotated by time and divided into 24 sections, each section representing a period of time of one hour. A highlighted circle 203 at a glucose level of 240 mg/dL marks a critical threshold of the glucose concentration which should not be exceeded. When a glucose level of more than 100 mg/dL is measured at a certain time, an appropriate point is plotted in the polar coordinate graphing system, where measurements following one another are connected by a line, which optionally can be interpolated providing a smoother curve. Measurements of glucose levels of less than 100 mg/dL lead to a point in the origin of this polar coordinate graphing system as there is no negative radial axis. In this coordinate system a radian of 2π represents a fixed period of elapsed time of the last 24 hours. An indicator 210 indicates the time of the measurement plotted most recently and therefore indicates the progress in plotting the measured data 205, similarly to a usual watch. Data being older than one cycle i.e. a radian of 2π e.g. representing 24 hours is substituted so always the recent 24 hours are displayed without possibly disturbing data measured earlier.

The invention is not limited to the embodiments described above. Other combinations of the visualisation method and/or the appropriate device may be used as well. Particularly, the visualisation method might be adapted to the display device, e.g. to its size and shape as well as to ways of communication between the measuring unit, computing device and display. The principal of a fixed period of elapsed time relating to a radian of 2π as shown in FIG. 6 with real-time indication/plotting of measured values is not restricted to the curve 205 but is also applicable to any other curve such as those plotted in FIGS. 4 or 5. The glucose meter can be a hand held or a strip based glucose meter, a combination of these or any other device being capable of measuring blood glucose levels or/and other glucose levels e.g. glucose levels measured in the interstitial fluid. Similar devices can be used as measuring units for other parameters such as e.g. a thermometer for body temperature, a sphygmomanometer for blood pressure or a pulse monitor for heart rate.

In summary, it is to be noted that the invention provides a method as well as a device, which enables both the patient and the physician or HCP to improve their recognition of important and/or periodic events during a chronological sequence of measurements in or on the human body, in particular during continuous glucose measurements.

What is claimed is:

1. A method for visualizing a chronological sequence of measurements comprising:
   receiving measured data from a continuous glucose monitoring process for a measured parameter;
   transforming, automatically with a computing unit, the measured data into presented measured data; and
   presenting the presented measured data with a display communicably coupled to the computing unit wherein:
   first values of the presented measured data above a first reference value are plotted by the computing unit in a first polar coordinate system;
   second values of the presented measured data below a second reference value are plotted by the computing unit in a second polar coordinate system;
   the second polar coordinate system having a differently and oppositely scaled radial axis from a radial axis of the first polar coordinate system but with both a common point of origin and a common circular axis with the first polar coordinate system;
   the first and second polar coordinate systems are displayed simultaneously by the computing unit, such that the second polar coordinate system is laid over the first polar coordinate system; and
   remaining values of the presented measured data below the first reference value and above the second reference value being plotted as a point in the common point of origin, wherein the first reference value of the first polar coordinate system is a different value from the second reference value of the second polar coordinate system.

2. The method as recited in claim 1, further comprises plotting time along the circular axis.

3. The method as recited in claim 2, further comprises representing as a radian of 2π a measurement pattern of 12 hours or 24 hours.

4. The method as recited in claim 2, wherein a radian of $2\pi$ represents a fixed period of elapsed time and said method further comprises displaying data of the fixed period of elapsed time.

5. The method as recited in claim 4, further comprises interpolating the presented measured data to build a smooth curve.

6. The method as recited in claims 5, further comprises displaying in color or grey shade an area between the origin of the first coordinate system and the smooth curve.

7. The method as recited in claim 6, further comprises having the color or grey shade show a transparency such that multiple coverings of the area in subsequent revolutions leads to gradual darkening of the area.

8. The method as recited in claim 6, further comprises transmitting the measured data via a communication link, wherein the communication link comprises a wireless transmission device with a sending and a receiving part; and the display is a mobile phone display, MP3player display, handheld computer display, laptop computer display, or personal computer.

9. The method as recited in claim 4, wherein the fixed period of elapsed time is switchable between 12 hours, 24 hours, a week, and a month.

10. The method as recited in claim 1, further comprises plotting numerical values of the presented measured data along the scaled radial axis, wherein the numerical values comprise a monitored glucose concentration.

11. The method as recited in claim 1, further comprises highlighting graphically a critical boundary as a highlighted circle that is fixed over time, wherein the critical boundary comprises a threshold for hyperglycemia or hypoglycemia.

12. The method as recited in claim 11, further comprises representing different numerical ranges of the numerical values that are target values by different colors or grey shades.

13. The method as recited in claim 1, further comprises displaying a difference to at least one of the first and second reference values or a modulus of the difference to at the least one of the first and second reference values.

14. The method as recited in claim 1, further comprises plotting time along the circular axis, wherein the time is selected from hours per day, days per week, weeks per month and combinations thereof.

15. The method as recited in claim 1, further comprises averaging previously recorded and stored data for the measured parameter and displaying on the display a resulting average curve from the averaging of the previously recorded and stored data along with the presented measured data.

16. A method for visualizing a chronological sequence of measurements comprising:
receiving measured data from a continuous glucose monitoring process for a measured parameter;
transforming, automatically with a computing unit, the measured data into presented measured data; and
presenting the presented measured data with a display communicably coupled to the computing unit wherein:
first values of the presented measured data above a first reference value are plotted by the computing unit in a first polar coordinate system;
second values of the presented measured data below a second reference value are plotted by the computing unit in a second polar coordinate system having a differently and oppositely scaled radial axis from a scaled radial axis of the first polar coordinate system but with both a common point of origin and a common circular axis with the first polar coordinate system;
the first and second polar coordinate systems are displayed simultaneously by the computing unit, such that the second polar coordinate system is laid over the first polar coordinate system;
the scaled radial axis of the first polar coordinate system increases radially;
the differently and oppositely scaled radial axis of the second coordinate system decreases radially; remaining values of the presented measured data below the first reference value and above the second reference value are plotted as a point in the common point of origin; and
first and second critical threshold values are each plotted by the computing unit as a highlighted circle that is fixed over time,
wherein the first values plotted and the first critical threshold value have the same units and relate to the same measured parameter, and in which the first critical threshold value is a value greater than the first reference value,
wherein the second values plotted and the second critical threshold value have the same units and relate to the same measured parameter, and in which the second critical threshold value is a value less than the second reference value, and
wherein the first reference value of the first coordinate system is a different value from the second reference value of the second coordinate system.

17. A method for visualizing a chronological sequence of measurements comprising:
receiving measured data from a continuous glucose monitoring process for a measured parameter, wherein the measured parameter is a glucose level;
transforming, automatically with a computing unit, the measured data into presented measured data; and
presenting the presented measured data with a display communicably coupled to the computing unit via the computing unit:
plotting first values of the presented measured data in a first polar coordinate system,
plotting second values of the presented measured data in a second polar coordinate system,
displaying simultaneously the first and second polar coordinate systems such that the second polar coordinate system is laid over the first polar coordinate system with a common point of origin, wherein:
a radial axis of the first polar coordinate system increases radially,
a radial axis of the second polar coordinate system decreases radially,
the first values plotted in the first polar coordinate system are above a first reference value that indicates hyperglycemia,
the second values plotted in the second polar coordinate system are below a second reference value that indicates hypoglycemia,
the first values plotted and the first reference value have the same units and relate to the same measured parameter,
the second values plotted and the second reference value have the same units and relate to the same measured parameter, and
the first reference value of the first polar coordinate system is a different value from the second reference value of the second polar coordinate system, and
plotting first and second critical threshold values each as a highlighted circle that is fixed over time, plotting remaining values of the presented measured data below the first reference value and above the second reference value as a point in the common point of origin;

plotting time along a circular axis in which a radian of $2\pi$ represents a fixed period of elapsed time, permitting periodicity of the circular axis to be switchable from a hours per day, days per week, weeks per month, and combinations thereof, displaying a difference to at least one of the first and second reference values or a modulus of the difference to at least one of the first and second reference values, and representing different numerical ranges of the first and second values that are target values by different colors or grey shades.

18. The method as recited in claim 17, further comprises interpolating the presented measured data to build a smooth curve.

19. The method as recited in claims 18, further comprises displaying in color or grey shade an area between the origin of the first polar coordinate system and the smooth curve.

20. The method as recited in claim 19, further comprises having the color or grey shade show a transparency such that multiple coverings of the area in subsequent revolutions leads to gradual darkening of the area.

* * * * *

UNITED STATES PATENT AND TRADEMARK OFFICE
CERTIFICATE OF CORRECTION

| | | |
|---|---|---|
| PATENT NO. | : 8,684,929 B2 | Page 1 of 1 |
| APPLICATION NO. | : 11/956840 | |
| DATED | : April 1, 2014 | |
| INVENTOR(S) | : Kelly Heaton | |

It is certified that error appears in the above-identified patent and that said Letters Patent is hereby corrected as shown below:

In the Specification

Col. 7, Line 11,
  "patient depend on events such a meal or physical activities," should read
  --patient depend on events such as a meal or physical activities,--;

In the Claims

Col. 11, Line 8, Claim 6,
  "The method as recited in claims 5, further comprises" should read
  --The method as recited in claim 5, further comprises--;

Col. 11, Line 39, Claim 13,
  "reference values or a modulus of the difference to at the least" should read
  --reference values or a modulus of the difference to the at least--; and Col. 13, Line 20, Claim 19,
  "19. The method as recited in claims 18, further comprises" should read
  --19. The method as recited in claim 18, further comprises--.

Signed and Sealed this
Twenty-fourth Day of February, 2015

Michelle K. Lee
*Deputy Director of the United States Patent and Trademark Office*